(12) United States Patent
Kawana

(10) Patent No.: US 7,305,866 B2
(45) Date of Patent: Dec. 11, 2007

(54) MASS SPECTROMETRY

(75) Inventor: Shuichi Kawana, Kyoto (JP)

(73) Assignee: Shimadzu Corporation, Kyoto-Shi, Kyoto (JP)

( * ) Notice: Subject to any disclaimer, the term of this patent is extended or adjusted under 35 U.S.C. 154(b) by 133 days.

(21) Appl. No.: 11/391,432

(22) Filed: Mar. 29, 2006

(65) Prior Publication Data

US 2006/0218990 A1      Oct. 5, 2006

(30) Foreign Application Priority Data

Mar. 31, 2005   (JP)   ............................. 2005-104885

(51) Int. Cl.
*G01N 30/02*   (2006.01)
*G01N 30/90*   (2006.01)

(52) U.S. Cl. .................. 73/23.37; 73/23.41; 95/82; 422/89; 436/161

(58) Field of Classification Search ................ 73/23.37, 73/23.41; 95/82; 422/89; 436/161

See application file for complete search history.

(56) References Cited

U.S. PATENT DOCUMENTS

| | | | | |
|---|---|---|---|---|
| 3,898,837 A | * | 8/1975 | Boege | ....................... 73/23.36 |
| 4,835,708 A | * | 5/1989 | Frans | ........................... 702/27 |
| 5,436,166 A | * | 7/1995 | Ito et al. | ....................... 436/161 |
| 5,939,612 A | * | 8/1999 | Wylie et al. | ............... 73/23.36 |

* cited by examiner

*Primary Examiner*—Daniel S. Larkin
(74) *Attorney, Agent, or Firm*—Manabu Kanesaka

(57) ABSTRACT

A method of gas chromatograph mass spectrometry with a negative chemical ionization (NCI) process includes analyzing a standard substance for the NCI by deriving with a derivatization reagent a fatty acid with a multiple number of carbon atoms, measuring the standard substance for the NCI by negative chemical ionization, and obtaining a retention time for each of the number of carbon atoms. The method includes measuring, under a same condition, a standard sample of each of from one to a plurality of measurement object components by negative chemical ionization, and obtaining a respective retention time for each of the measurement object components, and obtaining a retention index for the NCI of each measurement object component using the respective retention time of the measurement object component, and the retention time of the standard substance. The index facilitates both correcting the retention time of each measurement object component, and identifying substances.

4 Claims, 1 Drawing Sheet

---

A saturated fatty acid with a different number of carbons is derived by a PFB-Br (step 1)

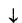

A derived saturated fatty acid (standard substance for NCI) is measured by an NCI method and retention time is obtained (step 2)

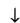

A standard sample of each measurement object component is measured by the NCI method and the retention time is obtained (step 3)

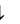

A retention index for the NCI of each measurement object component is obtained by the retention time of each measurement object component, as a standard of the retention time of the standard substance for the NCI (step 4)

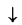

The retention time of each measurement object component is predicted using the retention index for the NCI (step 5)

| A saturated fatty acid with a different number of carbons is derived by a PFB-Br (step 1) |

| A derived saturated fatty acid (standard substance for NCI) is measured by an NCI method and retention time is obtained (step 2) |

| A standard sample of each measurement object component is measured by the NCI method and the retention time is obtained (step 3) |

| A retention index for the NCI of each measurement object component is obtained by the retention time of each measurement object component, as a standard of the retention time of the standard substance for the NCI (step 4) |

| The retention time of each measurement object component is predicted using the retention index for the NCI (step 5) |

MASS SPECTROMETRY

BACKGROUND OF THE INVENTION AND RELATED ART STATEMENT

The present invention relates to gas chromatograph mass spectrometry.

A gas chromatograph mass spectrometer (GC/MS) which is a combination of a gas chromatograph and a mass spectrometer is widely applied as an all-purpose analyzer which combines the high separation ability of the gas chromatograph and the excellent qualitative ability of the mass spectrometer. In the GC/MS, a mixture sample of an organic compound is separated by the gas chromatograph; elution gas of the gas chromatograph is guided to the mass spectrometer; and the mass spectrometer defines the component and determination.

For measuring the compound with the GC/MS, He (helium) and so on are used as the carrier gas of the gas chromatograph. The component which is separated at the column and eluted is ionized by an electron-impact ionization method (EI method) and so on, and the mass of the component is detected after being separated by the mass spectrometer. Accordingly, a mass chromatogram, a total ion chromatogram, or a mass spectrum is obtained. Thereafter, the determination can be conducted from a peak area and so on of a chromatogram, or the component can be determined by retention time, through a well-known method in the field of gas chromatography. Also, the component of the mass spectrum can be determined using a data base such as the NIST or the Wiley through a well-known method in the field of mass analysis.

Usually, in the field of gas chromatography, identification of an unknown component is conducted as follows. A standard sample of the measurement object component which is predicted to be contained is measured under a completely identical condition with the measurement of the unknown component, and identified by agreeing with the respective retention time. However, since the standard sample of each component has to be provided, dozens of standard samples have to be provided when many components are determined, and there are some substances which are difficult to obtain.

Also, the retention time in the gas chromatography differs from a wave length by a spectral analysis or a mass number by the mass analysis. The retention time is not the value which is unambiguously predicted based on properties of matter of the component substance, but is determined by many factors such as the type or size of the column, the temperature, the type, or pressure and flow of the carrier gas, and also the difference of an apparatus and so on. Therefore, even if an identical analysis condition is established, since a model of the apparatus, or conditions of the room temperature or the column and so on differs, there are no completely identical conditions. As a result, the retention time sometimes differs. In other words, even if the identical condition is established, not only when the flow or temperature is changed, but also when the apparatus or column is exchanged, or long periods have passed, the retention time changes. As a result, the standard sample of the measurement object component is required to be measured and the retention time is required to be re-measured.

Thus, conventionally, in order to eliminate the above-mentioned variable factors as much as possible, a retention index is used for the identification of the component. The retention index is an index which indexes the retention time of each component substance by the retention time of the predetermined standard substance (generally, n-alkane), and is unaffected by the difference of a GC condition, a column manufacturer, length, inside diameter, or film thickness and so on. Therefore, without having to measure the standard sample of the measurement object component, if the retention index of the measurement object component is determined, the component can be identified by obtaining and comparing the retention index of the unknown component. As a result, the standard sample is not required to be measured. (For example, see *Journal of Chromatography*, 91 (1074) 89-103.)

In addition to the EI method, an ionization method in mass analysis is a method in which reaction gas (methane, isobutene, ammonia, etc.) is introduced into an ionization chamber, and the reaction gas is ionized by an electron impact and so on. At the same time, the ionization method forms a negative ion by electron capture of an emitted electron. As described above, the chemical ionization such that the negative ion is formed is known as the Negative Chemical Ionization (NCI) method.

Since the electron is selectively introduced into the substance with high electron affinity in the NCI method, the compound with high electron affinity is selectively negatively-ionized. As a result, the influence of a sandwiched incidental material can be reduced, and sometimes, sensitivity to a certain type of compound can be improved approximately 10-100 times compared with the EI method which is usually used. The NCI method is used for the determination of a minor constituent in a variety of areas because of high selectability or high sensitivity as described above. However, capabilities of the identification and determination of the component by a mass spectrum of the NCI method is considered to be inferior to the EI method.

Ionization by the NCI method is known as an ionization method which is suitable for selectively ionizing a halogen compound and so on with a high electron affinity and measuring with high sensitivity. However, compared to the mass spectrum in the EI method, the mass spectrum in the NCI method has fewer fragment ions and the spectral pattern is easier. Also, depending on the condition at the time of the ionization, the pattern of the mass spectrum sometimes differs slightly, and the identification ability by the mass spectrum is considered to be inferior to that of the mass spectrum in the EI method. Therefore, in order to enhance the reliability of the identification, the confirmation of the agreement of the retention time which is a conventional technology is effective.

However, as mentioned above, in order to confirm the agreement of the retention time, the standard sample of the measurement object component which is predicted to be contained is measured, and the agreement of the retention time of the chromatogram is confirmed. Accordingly, the standard sample has to be provided for each component to be measured, so that when multiple components are analyzed, the variety is enormous, and sometimes it is difficult to obtain, or it can be very expensive. In addition, since the retention time changes depending on the model of the apparatus or by cutting the column, the standard sample is frequently required to be measured.

Furthermore, the method described in conventional technology in which the standard sample is not measured and the retention index is used is not available when the measurement is performed by the NCI method in the GC/MS. Generally, the retention index is defined by the retention time of the n-alkane; however, when the measurement is performed by the NCI method, the n-alkane is not detected, and the retention time of the n-alkane under the same condition with an unknown sample is not known. Therefore, the retention index of the unknown sample cannot be obtained, so that the identification of the chromatogram by the retention index without the analysis of the standard sample is impossible.

The present invention was developed in order to solve the above-described problems. An object of the invention is to frequently provide the standard sample of a measurement object component by a "retention index for the NCI" which can be used when a GC/MS analysis is conducted using the NCI method, and to conduct a determination of the component with high reliability by retention time information without any analysis.

Further objects and advantages of the invention will be apparent from the following description of the invention.

SUMMARY OF THE INVENTION

In order to solve the above-described problems, gas chromatograph mass spectrometry with negative chemical ionization according to the present invention includes the following two processes. One process analyzes: a standard substance for the NCI in which a fatty acid with a different number of carbons is derived by a derivatization reagent; a standard substance for the NCI; and from one to multiple standard samples, under the same condition, and obtains each retention time.

The other process obtains a retention index for the NCI of each standard substance using the respective retention time.

The present invention is also a data base for a gas chromatograph mass analysis instrument using negative chemical ionization.

The standard substance for the NCI in which the fatty acid with a different number of carbons is derived by the derivatization reagent, and the standard samples of from one to multiple substances, are analyzed under the same condition. The retention index for the NCI of each substance which is obtained from the respective retention time includes the information related to the name of the substance. For "the fatty acid with a different number of carbons" described in the present invention, for example, a saturated fatty acid or an unsaturated fatty acid with 4-30 carbons may be used. Specifically, it means, for example, a butyric acid or isobutyric acid. For the derivatization reagent, for example, PFB (pentafluorobenzyl), TFA (trifluoroacyl), PFP (pentafluoropropionyl), or HFB (pentafluorobutyryl) may be used.

According to the invention, in the GC/MS with the NCI method, in order to predict the retention time when a substance is analyzed under a condition, if the "retention index for the NCI" is already known, the retention time under the condition can be predicted by measuring the "standard substance for the NCI" without analyzing the standard sample.

Also, in the GC/MS with the NCI method, the component can be identified more precisely by using the mass spectrum of the NCI and the "retention index for the NCI."

Furthermore, in the GC/MS with the NCI, when the spectrum of an unknown sample is searched by an NCI library, a candidate can be narrowed by the "retention index for the NCI."

BRIEF DESCRIPTION OF THE DRAWINGS

The drawing is a flowchart of the gas chromatograph mass spectrometer process according to the present invention.

DETAILED DESCRIPTION OF THE PREFERRED EMBODIMENTS

Hereinafter, an embodiment of the present invention will be explained with reference to the drawing. A saturated fatty acid with a different number of carbons is derived by a PFB-Br (Pentafluorobenzyl bromide) (step 1). Hereinafter, the structural formula of the PFB-Br is shown.

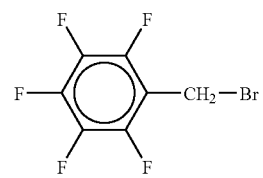

Hereinafter, an example of a method of derivatization by the PFB-Br will be shown. In the example, 5 ul of PFB-Br, 10 ul of triethylamine, and 50 ul of acetonitrile are mixed into a saturated fatty acid with a different number of carbons, are heated at 80° C. for 30 minutes, then washed with 0.5 ml of 0.1 mol/l HCl, and then extracted with 1.5 ml of hexane. A fatty acid with the number n of carbons is derived as a formula (1).

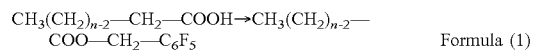    Formula (1)

Herewith, the saturated fatty acid with the different number of carbons is derived by the PFB-Br, and the mixture of the saturated fatty acid with the different number of carbons which is derived by the PFB-Br is used as a "standard substance for the NCI." For example, the saturated fatty acid with 4-10 carbons is respectively derived, and the mixture is used as the "standard substance for the NCI."

The embodiment is derived by the PFB-Br; however, the method and reagent of the derivatization are not limited to the derivatization by the PFB-Br, and a well-known method which is detected by the NCI method may be used.

The "standard substance for the NCI" obtained by the above-mentioned method is measured by the GC/MS with the NCI method, and the retention time is obtained for every number of carbons (step 2). The standard sample of each measurement object component is also measured by the completely same condition, and the retention time of respective components is obtained (step 3). Based on the "standard substance for the NCI" and the retention time of each measurement object component, each "retention index for the NCI," in which the "standard substance for the NCI" is the standard substance, is obtained for each measurement object component (step 4).

At this time, it is important that step 2 and step 3 are performed under the completely same analytical condition. For example, measurements in step 2 and step 3 may be performed closely in terms of time, or the "standard substance for the NCI" and each measurement object component may be mixed and measured.

The "retention index for the NCI" can be obtained by replacing the number of carbons of the saturated fatty acid by the number of carbons of the n-alkane (z in formulas 2, 3), according to the method of obtaining a "retention index for the n-alkane" in which an n-alkane is conventionally used as the standard substance. The "retention index for the NCI" is the characteristic value of each substance in the same way as the "retention index for the n-alkane." For example, according to the *Journal of Chromatography*, 91

(1074) 89-103, the retention index for the n-alkane is defined by the formula (2) in the case of a constant temperature analysis, and by the formula (3) in the case of a temperature rise analysis.

$$I = 100\left(\frac{\log V_{N(x)} - \log V_{N(z)}}{\log V_{N(z+1)} - \log V_{N(z)}} + z\right) \quad \text{Formula (2)}$$

$$I_{PTGC} = 100\left(\frac{T_{r(x)} - T_{r(z)}}{T_{r(z+1)} - T_{r(z)}} + z\right) \quad \text{Formula (3)}$$

As described above, if the "retention index for the NCI" of some standard substance is obtained, the "standard substance for the NCI" is measured under the condition of intending to measure a real sample, and the retention time of the "standard substance for the NCI" is obtained. The retention time of the measurement object component under the condition of intending to measure the real sample can be predicted by the retention time of the "retention index for the NCI" of the measurement object component and the "standard substance for the NCI".

Also, the "retention index for the NCI" may be obtained by each measurement object component, and that may be a data base by correlating the "retention index for the NCI" with the name of the substance, or an NCI mass spectrum.

When the unknown sample is analyzed, an analytical condition is established, the "standard substance for the NCI" is measured, and the retention time is obtained. After that, with no change in the analytical condition, the unknown sample is also measured, and the retention time is obtained. At this time, it is important that the "standard substance for the NCI" and the unknown sample have to be measured under the completely same condition. For example, the measurement may be performed by combining the unknown sample with the "standard substance for the NCI." From the obtained retention time of the "standard substance for the NCI" and the unknown sample, the "retention index for the NCI" of the unknown sample is obtained.

Without providing the standard substance of each measurement object component, the "retention index for the NCI" of the unknown sample and the "retention index for the NCI" of each component can be compared and the unknown sample can be identified.

Also, if the data base is made by correlating the NCI mass spectrum and the "retention index for the NCI" with the name of the substance by each measurement object component, when the component of the unknown sample is determined and identified in the GC/MS with the NCI method, the determination of the component and identification with additional high reliability can be also conducted by using the data of the NCI mass spectrum and the "retention index for the NCI" at the same time.

Incidentally, all the above-mentioned embodiments are but one example of the present invention, and can be accordingly changed or modified provided that they do not exceed the subject matter of the present invention. For example, the present invention may be derived by TFA (trifluoroacyl), PFP (pentafluoropropionyl), or HFB (pentafluorobutyryl) and so on, and may be the "standard substance for the NCI."

The disclosure of Japanese Patent Application No. 2005-104885 filed on Mar. 31, 2005, is incorporated herein.

What is claimed is:

1. A method of gas chromatograph mass spectrometry with a negative chemical ionization (NCI) process, comprising:

analyzing a standard substance for the NCI by deriving with a derivatization reagent a fatty acid with a multiple number of carbon atoms;

measuring the standard substance for the NCI by negative chemical ionization, and obtaining a retention time for each of the number of carbon atoms;

measuring, under a same condition, a standard sample of each of from one to a plurality of measurement object components by negative chemical ionization, and obtaining a respective retention time for each of the measurement object components; and obtaining a retention index for the NCI of each measurement object component using the respective retention time of the measurement object component, and the retention time of the standard substance.

2. A method according to claim 1, further comprising correcting the retention time of each measurement object component by using the retention index for the NCI.

3. A method according to claim 1, further comprising identifying a substance by using the retention index for the NCI.

4. A method of providing a data base for a gas chromatograph mass spectrometer with a negative chemical ionization (NCI) process, comprising:

analyzing a standard substance for the NCI by deriving with a derivatization reagent a fatty acid with a multiple number of carbon atoms;

measuring the standard substance for the NCI by negative chemical ionization, and obtaining a retention time for each of the number of carbon atoms;

measuring, under a same condition, a standard sample of each of from one to a plurality of measurement object components by negative chemical ionization, and obtaining a respective retention time for each of the measurement object components;

obtaining a retention index for the NCI of each measurement object component using the respective retention time of the measurement object component, and the retention time of the standard substance; and correlating the retention index for the NCI of each measurement object component with a name of a corresponding substance.

* * * * *